US006465626B1

United States Patent
Watts et al.

(10) Patent No.: US 6,465,626 B1
(45) Date of Patent: Oct. 15, 2002

(54) PHARMACEUTICAL COMPOSITIONS OF CHITOSAN WITH TYPE-A GELATIN

(75) Inventors: Peter James Watts; Lisbeth Illum, both of Nottingham (GB)

(73) Assignee: West Pharmaceutical Services Drug Delivery and Clincal Research Centre, Limited, Nottingham (GB)

( * ) Notice: Subject to any disclaimer, the term of this patent is extended or adjusted under 35 U.S.C. 154(b) by 0 days.

(21) Appl. No.: 09/341,546

(22) PCT Filed: Jan. 14, 1998

(86) PCT No.: PCT/GB98/00108

§ 371 (c)(1),
(2), (4) Date: Aug. 18, 1999

(87) PCT Pub. No.: WO98/30207

PCT Pub. Date: Jul. 16, 1998

(30) Foreign Application Priority Data

Jan. 14, 1997 (GB) ............................................. 9700624

(51) Int. Cl.[7] .......................... C08B 37/08; A01N 43/04
(52) U.S. Cl. ........................................... 536/20; 514/55
(58) Field of Search ............................... 514/55; 536/20

(56) References Cited

U.S. PATENT DOCUMENTS 4,226,849 A   10/1980   Schor

FOREIGN PATENT DOCUMENTS

| EP | 023 359 A2 | 10/1981 |
| EP | 122 023 A1 | 10/1984 |
| EP | 376 385 A2 | 7/1990 |
| EP | 454 444 A1 | 10/1991 |
| EP | 470 872 A1 | 2/1992 |
| EP | 486 959 A1 | 5/1992 |
| WO | WO 88/09163 A1 | 12/1988 |
| WO | WO 89/03207 A1 | 4/1989 |
| WO | WO 90/09780 A1 | 9/1990 |
| WO | WO 91/11175 A1 | 8/1991 |
| WO | WO 96/03142 A1 | 2/1996 |
| WO | WO 96/05810 A1 | 2/1996 |
| WO | WO 96/10421 A1 | 4/1996 |
| WO | WO 97/05903 A2 | 2/1997 |

OTHER PUBLICATIONS

Allan & Peyron, "Molecular weight manipulation of chitosan. I: Kinetics of depolymerization by nitrous acid," *Carbohydr. Res.* 277(2):257–72 (1995).

Bodmeier, et al., "A novel approach to the oral delivery of micro–or nanoparticles," *Pharm. Res.* 6(5):413–17 (1989).

Cortesi, et al., "Gelatin microspheres as a new approach for the controlled delivery of synthethic oligonucleotides and PCR–generated DNA fragments," *Int. J. Pharm.* 105:181–86 (1994).

Davis, et al., *Delivery Systems for Peptide Drugs*, Plenum Press:New York, 1986, Table of Contents Only.

Domard & Cartier, "Glucosamine oligomers: 1. Preparation and characterization," *Int. J. Biol. Macromol.* 11(5):297–02 (1989).

Esposito, et al., "Controlled release of 1–β–D–arabinofuranosylcytosine (ara–C) from hydrophilic gelatin microspheres: in vitro studies," *Int. J. Pharm.* 117:151–58 (1995).

Healey, "Enteric Coatings and Delayed Release" in *Drug Delivery to the Gastrointestinal Tract* (Hardy, et al., eds.) Ellis Horwood: Chichester, 1989.

Jameela & Jayakrishnan, "Glutaraldehyde cross–linked chitosan microspheres as a long acting biodegradable drug delivery vehicle: studies on the in vitro release of mitoxantrone and in vivo degradation of microspheres in rat muscle," *Biomaterials.* 16(10):769–75 (1995).

Lee, et al., *Peptide and Protein Delivery*, Marcel Dekker, Inc.:New York, 1991, Table of Contents Only.

Li, et al., "Polysaccharide microcapsules and macroporous beads for enhanced chromatographic separation," *Biomater. Artif. Cells & Immobilization Biotechnol.* 21(3):391–98 (1993).

Li, et al., "Enzymatic production of chitosan oligomers," *Plant Physiol. Biochem.* 33:599–603 (1995).

Machida, et al., "Development of topical drug delivery systems utilizing polymeric materials," *Yakugaku Zasshi.* 113(5):356–68 (1993).

Nagai, et al., "Application of chitin and chitosan to pharmaceutical preparations," in *Chitin, Chitosan and Related Enzymes* (Zikakis, ed.) pp. 21–39, Academic Press:Orlando, 1984.

Nastruzzi, et al., "Production and in vitro evaluation of gelatin microspheres containing an antitumour tetra–amidine," *J. Microencapsul.* 11(3):249–60 (1994).

Ohya, et al., "Release behaviour of 5–fluorouracil from chitosan–gel microspheres immobilizing 5–fluorouracil derivative coated with polysaccharides and their cell specific recognition," *J. Microencapsul.* 10(1):1–9 (1993).

Polk, et al., "Controlled release of albumin from chitosan–alginate microcapsules," *J. Pharm. Sci.* 83(2):178–85 (1994).

(List continued on next page.)

Primary Examiner—Kathleen Kahler Fonda
(74) Attorney, Agent, or Firm—Akin, Gump, Strauss, Hauer & Feld, L.L.P.

(57) ABSTRACT

A drug delivery composition for nasal administration is provided which comprises the antiviral agent ICAM-1 and a bioadhesive material. The bioadhesive material may be a chitosan solution, a liquid formulation comprising a polymeric material or a plurality of bioadhesive microspheres. The polymeric material is preferably gellan gum or alginate. The microspheres may comprise starch, chitosan, hyaluronic acid, or gelatin.

43 Claims, 8 Drawing Sheets

OTHER PUBLICATIONS

Remunan–Lopez & Bodmeier, "Effect of formulation and process variables on the formation of chitosan–gelatin coacervates," *Int. J. Pharm.* *135*:63–72 (1996).

Sawayanagi, et al., "Dissolution properties and bioavailability of phenytoin from ground mixtures with chitin or chitosan," *Chem. Pharm. Bull.* *31*:2064–68 (1983).

Tabata, et al, "Synthesis of gelatin microspheres containing interferon," *Pharm. Res.* *6*(5):422–27 (1989).

Thanoo, et al., "Cross–linked chitosan microspheres: preparation and evaluation as a matrix for the controlled release of pharmaceuticals," *J. Pharm. Pharmacol.* *44*(4):283–86 (1992).

Van Den Mooter, "Azo polymers for colon–specific drug delivery," *Int. J. Pharm.* *87*:37–46 (1992).

PHARMACEUTICAL COMPOSITIONS OF CHITOSAN WITH TYPE-A GELATIN

Priority is claimed under 35 U.S.C. §119 to PCT/GB98/00108, filed Jan. 14, 1998, which corresponds to GB 97/00624.1 filed Jan. 14, 1997.

This invention relates to novel drug delivery compositions which provide for the improved uptake of therapeutic agents across mucosal surfaces.

Polar drugs, including high molecular weight peptides, proteins and polysaccharides, are typically not effectively absorbed across mucosal membranes, such as the gastrointestinal tract, the eye, the vagina, the nasal cavity or the rectum. Such molecules are thus normally only given by injection, which inevitably gives rise to well known problems associated with patient compliance, the cost of treatment, as well as the potentially harmful effects, such as phlebitis and pain, of the injection.

It is well known in the literature that the absorption of polar molecules across mucosal membranes may be greatly improved if they are administered in combination with so-called "absorption enhancers". Examples of absorption enhancers which have been described in the literature include non-ionic surfactants, cyclodextrins, pholspholipids and bile salts. (For a review see Davis et al (eds.), Delivery Systems for Peptide Drugs, Plenum Press, New York, 1987; and Lee (ed.), Peptide and Protein Delivery, Marcel Dekker Inc., New York, 1991.)

EP-A-023 359 and EP-A-122 023 describe powdery pharmaceutical compositions for application to the nasal mucosa, as well as methods for the administration of such compositions. The pharmaceutical compositions allow polypeptides and derivatives thereof to be effectively absorbed through the nasal mucosa. Similarly, U.S. Pat. No. 4,226,849 describes a method for administering a powdery medicament to the nasal mucosa, in which the preferred composition has mucoadhesive properties.

Formulations based on microspheres for mucosal delivery have been described in WO 88/09163. The formulations contain certain enhancers to aid effective penetration of the mucosa by the drug. WO 89/03207 describes microsphere formulations which do not require an enhancer.

Chitosan is a derivative of chitin or poly-N-acetyl-D-glucosamine in which the greater proportion of the N-acetyl groups have been removed through hydrolysis. It is available from several suppliers including Pronova, Drammen, Norway, and, depending on the grade selected, is soluble in water and/or aqueous acid up to pH values of between 6.0 and 7.0.

Chitosan has previously been used to precipitate proteinaceous material and to make surgical sutures. It has also been employed previously in oral drug formulations in order to improve the dissolution of poorly soluble drugs (see Sawavanagi et al, Chem. Pharm. Bull., 31 (1983) 2062–2068) or for the sustained release of drugs by a process of slow erosion from a hydrated compressed matrix (Nagai et al, Proc. Jt. US Jpn. Semin. Adv. Chitin Chitosan Relat. Enzymes, 21–39, Zikakis J. P. (ed.), Academic Press, Orlando, 1984).

WO 90/09780 describes a composition comprising a drug and a polycationic substance (e.g. chitosan) that promotes the transport of the drug across mucosal membranes. The composition may also comprise microspheres of the polycationic substance.

WO 96/05810 describes a composition comprising a pharmacologically active compound and particles, preferably powders or microspheres, of chitosan or a chitosan derivative or salt, where the particles are either solidified or partially cross-linked such that they have a zeta-potential of between +0.5 and +50 mV. Solidified particles are made by treating particles made from a water soluble chitosan salt with an alkaline agent, such as sodium hydroxide, in non-acid containing water to render them insoluble.

Chitosan microspheres have also been produced for use in enhanced chromatographic separation (Li Q. et al, Biomater. Artif. Cells Immobilization Biotechnology, 21 (1993) 391–398), for the topical delivery of drugs (Machida Y., Yakugaku Zasshl., 113 (1993) 356–368), for drug targeting after injection (Ohya Y et al, J. Microencap., 10 (1993) 1–9), as an implantable controlled release delivery system (Jameela and Jayakrishnan, Biomaterials, 16 (1995) 769–775) and for the controlled release of drugs (see Bodmeier R. et al, Pharm. Res., 6 (1989) 413–417 and Chithambara et al, J. Pharm. Pharmacol., 44 1992, 283–286).

EP 454044 and EP 486959 describe polyelectrolyte microparticles or polysaccharide microspheres, including chitosan microspheres, for use in the controlled release of drugs. Chitosan microspheres crosslinked with glutaraldehyde have also been described in JP 539149.

Gelatin is a purified protein obtained either by partial acid hydrolysis (type A) or by partial alkaline hydrolysis (type B) of animal collagen. Type A gelatin is cationic with an isoelectric point between pH values of 7 and 9, whereas type B gelatin is anionic with an isoelectric point between pH values of 4.7 and 5. Gelatin is known to swell and soften when immersed in cold water, eventually absorbing between 5 and 10 times its own weight in water. It is soluble in hot water, forming a gel on cooling. Gelatin is used as a haemostatic in surgical procedures as an absorbable film or sponge, which can absorb many times its own weight in blood. It is also employed as a plasma substitute, and may be used in the preparation of pastes, pastilles, suppositories, tablets and hard and soft capsule shells for oral formulations.

The production of gelatin microspheres has been widely described in the literature. Gelatin microspheres have been produced by an emulsification method involving crosslinking with glutaraldehyde, producing microspheres of less than 2 μm in diameter (Tabata and Ikada, Pharm. Res. 6 (1989) 422–427). Cortesi et al (Int. J. Pharm. 105 (1994) 181–186), Natruzzi et al (J. Microencapsulation, 11 (1994) 294–260) and Esposito et al (Int. J. Pharm., 117 (1995) 151–158) have reported the production of microspheres of a mean diameter of 22 μm using a coacervation emulsification method. Microspheres as produced by the latter processes were not crosslinked. Microspheres of a smaller size have been produced according to a similar method by Esposito et al (Pharm. Sci. Commun. 4 (1994) 239–246). The type of gelatin (A or B) used in these studies was not specified.

The production of microspheres by complexation, between a negatively charged material such as alginate and a positively charged chitosan has been described in the literature. For example. Polk et al, J. Pharm. Sci., 83 (1994) 178–185) describes the production of clhitosan-alginate microspheres by the addition of an alginate solution to a solution of chitosan and calcium ions. The highest concentration of chitosan used in the microsphere formulations was 5.2% w/w. Similarly, the formation of complex coacervates between oppositely charged polyions, namely a positively charged chitosan and a negatively charged type B gelatin has been described by Remunan-Lopez and Bodmeier (Int. J. Pharm. 135 (1996) 63–72). These workers found the optimum chitosan:gelatin ratio to be in the range 1:10 to 1:20. The coacervate was obtained in a dry form by decanting the supernatant after centrifugation and drying at 60° C. We have now found, surprisingly, that microparticles, produced from a combination of a chitosan and a cationic type A gelatin, possess particularly advantageous properties, which enable the improved transport of therapeutic agents, including polar drugs, across mucosal surfaces such as the nasal cavity.

Thus, according to a first aspect of the invention there is provided a composition comprising a mixture of chitosan and type A. cationic, gelatin, together with a therapeutic agent (hereinafter referred to as "the compositions according to the invention").

By "mixture of chitosan and type A gelatin" we include any composition comprising a chitosan, as defined hereinafter, and a type A gelatin, as defined hereinafter, whether a physical and/or chemical association between these two constituents exists or not.

The term "chitosan" will be understood by those skilled in the art to include all derivatives of chitin, or poly-N-aceryl-D-glucosamine (including all polyglucosamine and oligomers of glucosamine materials of different molecular weights), in which the greater proportion of the N-acetyl groups have been removed through hydrolysis. We prefer that the chitosan has a positive charge.

Chitosan, chitosan derivatives or salts (e.g. nitrate, phosphate, sulphate, hydrochloride, glutamate, lactate or acetate salts) of chitosan may be used. We use the term chitosan derivatives to include ester, ether or other derivatives formed by bonding of acyl and/or alkyl groups with OH groups, but not the $NH_2$ groups, of chitosan. Examples are O-alkyl ethers of chitosan and 0-acyl esters of chitosan. Modified chitosans, particularly those conjugated to polyethylene glycol, are included in this definition. Low and medium viscosity chitosans (for example CL113, G210 and CL110) may be obtained from various sources, including Pronova Biopolymer, Ltd., UK; Seigagaku America Inc., Maryland, USA; Meron (India) Pvt, Ltd., India; Vanson Ltd, Virginia, USA; and AMS Biotechnology Ltd., UK. Suitable derivatives include those which are disclosed in Roberts, *Chitin Chemistry*, MacMillan Press Ltd., London (1992).

The chitosan or chitosan derivative or salt used preferably has a molecular weight of 4,000 Dalton or more, preferably in the range 25,000 to 2,000,000 Dalton, and most preferably about 50,000 to 300,000 Dalton. Chitosans of different low molecular weights can be prepared by enzymatic degradation of chitosan using chitosanase or by the addition of nitrous acid. Both procedures are well known to those skilled in the art and are described in recent publications (Li et al. (1995) Plant Physiol. Biochem. 33, 599–603; Allan and Peyron, (1995) Carbohydrate Research 277, 257–272; Damard and Cartier, (1989) Int. J. Biol. Macromol. 11, 297–302).

Preferably, the chitosan is water-soluble and may be produced from chitin by deacetylation to a degree of greater than 40%, preferably between 50% and 98%, and more preferably between 70% and 90%. Particular deacetylated chitosans which may be mentioned include the "Sea Cure®" series of chitosan glutamates available from Protan Biopolymer A/S, Drammen, Norway.

The term "type A gelatin" includes all cationic proteins which are, or may be, obtained by partial acid hydrolysis of animal collagen, and excludes type B gelatins.

Although the compositions according to the invention may be prepared in a variety of physical forms using techniques which will be well known to the skilled person, we prefer that the compositions are in the form of microparticles. The term "microparticles" includes microspheres, microcapsules and powders. However, we prefer that the microparticles are microspheres.

We have found, surprisingly, that when the compositions according to the invention are provided in the form of microparticles, such microparticles retain a positive charge and may provide for the improved transport of polar drugs across, or for the improved presentation of vaccines to muscosal surfaces, such as the nasal cavity, to such an extent that the effect is superior to that obtained for a chitosan solution, or microparticles produced from chitosan or type A gelatin alone (e.g. soluble (spray dried) chitosan microsphercs and gelatin microspheres). The effect is also similar to that obtained for partially aldehyde crosslinked chitosan microspheres, yet the compositions according to the invention are sufficiently hard/solid not to require crosslinking. We have further found that the flow properties of these chitosan/type A gelatin microparticles are superior to those of spray dried chitosan microspheres and crosslinked chitosan microspheres.

The microparticles may be prepared by spray drying, emulsification, solvent evaporation, precipitation or other methods known to a person skilled in the art. The therapeutic agent can be incorporated into the microparticles during their production or sorbed onto the microparticles after their production.

When the compositions according to the invention are in the form of microspheres, they may be prepared using for example either emulsification or spray drying techniques.

When microspheres are prepared by spray drying, a warm mixture of chitosan and type A gelatin is spray dried with instant cooling of the resultant microspheres. The therapeutic agent may be incorporated by adsorbing onto the surface of the microspheres by freeze drying or spray drying a suspension of the microspheres with the therapeutic agent, or by physically or mechanically mixing the dried microspheres with the therapeutic agent.

However, we have found that microspheres may advantageously be prepared by warming a solution of a chitosan mixed with type A gelatin which is then emulsified and gelated by cooling. We have found that, in particular, microspheres prepared in accordance with this technique exhibit the advantageous properties referred to hereinbefore.

In the emulsification technique, the chitosan may be dissolved in water and mixed with type A gelatin under heating to 40° C. causing the gelatin to melt. This mixture may be emulsified, at a temperature above the melting point of the gelatin, in an organic medium (e.g. a vegetable oil, such as sunflower oil, soya oil, cotton seed oil or coconut oil), in the presence of an emulsifier with a low hydrophilic-lipophilic balance (HLB) value. Such emulsifiers, which are useful for stabilising water-in-oil emulsions, are known to those skilled in the art (e.g. Span 80). The microspheres may then be solidified by decreasing the temperature of the emulsion to below 10° C. with stirring. The microspheres may then be harvested using conventional techniques, for example by adding a pharmaceutically acceptable organic solvent, e.g. chilled acetone or petroleum ether, to the emulsion, centrifugation, washing and drying. The therapeutic agent may be incorporated into the microspheres by adding it to the chitosan/gelatin mixture before emulsification. Alternatively, the therapeutic agent may be adsorbed onto the surface of the microspheres by freeze drying or by spray drying a suspension of the microsphercs with the therapeutic agent, or by physically or mechanically mixing the dried microspheres with the therapeutic agent.

Thus, according to a further aspect of the invention there is provided a drug delivery composition in a form suitable for administration to a mucosa comprising a therapeutic agent and microparticles made from a mixture of chitosan and type A gelatin and where the agent is either incorporated into the particles during production or is adsorbed to the surface of the particles, or is present as an admixture.

Microcapsules and powders may be made by modifying the process as defined herein in accordance with techniques which are well known to those skilled in the art, or may be prepared in accordance with other techniques which will be well known to those skilled in the art, including double emulsification processes.

According to a further aspect of the invention there is provided a process for the preparation of a composition according to the invention, which process comprises preparation of type A gelatin/chitosan microparticles (i.e. microparticles comprising a mixture of type A gelatin and chitosan) by a process of spray drying or by emulsification, which emulsification may comprise warming a solution of a chitosan mixed with type A gelatin, emulsification and gelation by cooling.

The flow properties of the microparticles can be measured by methods known to those skilled in the art. One possible method involves the measurement of the Hausner Ratio where a known weight of material is poured into a measuring cylinder and the volume recorded. The cylinder is then tapped against a surface a specified number of times and the volume again recorded. The poured and tapped densities are then determined and the Elausner Ratio=tapped density/poured density calculated. A ratio of <1.25 indicates a free flowing material while a ratio of >1.5 indicates a poor flowing (cohesive) material. Another possible method involves the measurement the Angle of Repose by pouring material through a funnel held at a fixed height onto a piece of graph paper until a cone is formed. The height (H) and the radius (R) of the cone is determined and the angle calculated (tan θ=H/R). An Angle of Repose θ<300 indicates good flow properties while an Angle of Repose θ>400 indicates very poor flow properties (James I. Wells, Pharmaceutical Preformulation, Ellis Horwood Series in Pharmaceutical Technology, 1988).

The size of the microparticles, which includes microcapsules and especially microspheres, is preferably in the range 1 to 200 μm, more preferably 1 to 100 μm, as measured by e.g. light microscopy or sieve fractionation.

The microparticles will consist of preferably between 50 and 95%, more preferably between 70 and 90% and most preferably between 75 and 85% of type A gelatin, and correspondingly between 50 and 5%, preferably between 30 and 10% and most preferably between 25 and 15% of chitosan, as measured in relation to the total amount of gelatin and chitosan in the final composition (i.e. excluding therapeutic agent and other ingredients which may be included).

The term "therapeutic agent" includes drugs, genes (DNA) or gene constructs, vaccines and components thereof (for example isolated antigens or parts thereof) and monoclonal antibodies. For applications employing such materials as genes, gene constructs, vaccines and monoclonal antibodies, the microparticles can be used to enhance the delivery of the therapeutic agent into the mucosal tissue for enhanced therapeutic effect, for example presentation of an antigen to the underlying lymphoid tissue, and/or transfection of the cells in the mucosal lining.

Preferably the therapeutic agent is a polar drug. By "polar drugs" we means molecules with a partition coefficient (octanol—water system) of less than 50.

The compositions may be used with therapeutic agents selected from the following non-exclusive list: insulin, PTH (parathyroid hormone), PTH analogues, PTHrP (human parathyroid hormone peptide), calcitonins (for example porcine, human, salmon, chicken or eel) and synthetic modifications thereof, enkephalins, LHRH (luteinising hormone releasing hormone) and analogues (nafarelin, buserelin, leuprolide, goserelin), glucagon, TRH (thyrotropine releasing hormone), vasopressin, desmopressin, growth hormone, heparins, GHRH (growth hormone releasing hormone), CCK (cholecystokinin), THF (thymic humoral factor), CGRP (calcitonin gene related peptide), atrial natriuretic peptide, nifedipine, metoclopramide, ergotamine, pizotizin, pentamidine and vaccines (particularly but not limited to AIDS vaccines, measles vaccines, rhinovirus Type 13 and respiratory syncytial virus vaccines, influenza vaccines, pertussis vaccines, meningococcal vaccines, tetanus vaccines, diphtheria vaccines, cholera vaccines and DNA vaccines (e.g. one containing a plasmid DNA coding for a suitable antigen)).

Further therapeutic agents include but are not limited to: antibiotics and antimicrobial agents, such as tetracycline hydrochloride, leucomycin, penicillin, penicillin derivatives, erythromycin, sulphathiazole and nitrofurazone; anti-migraine compounds, such as naratriptan, sumatriptan, alnitidan or other 5-HT1 agonists; vasoconstrictors, such as phenylephedrine hydrochloride, tetrahydrozoline hydrochloride, naphazolinie nitrate, oxymetazoline hydrochloride and tramazoline hydrochloride; cardiotonics, such as digitalis and digoxin; vasodilators, such as nitroglycerine and papaverine hydrochloride; bone metabolism controlling, agents, such as vitamin D and active vitamin D3; sex hormones; hypotensives; anti-tumour agents; steroidal anti-inflammatory agents, such as hydrocortisone, prednisone, fluticasone, prednisolone, triamcinolone, triamcinolone acetonide, dexamethasone, betamethasone, beclomethasone and beclomethasone dipropionate; non-steroidal anti-inflammatory agents, such as acetaminophen, aspirin, aminopyrine, phenylbutazone, mefanic acid, ibuprofen, diclofenac sodium, indomethacin, colchicine and probenecid; enzymatic anti-inflammatory agents, such as chymotrypsin and bromelain seratiopeptidase; anti-histaminic agents, such as dephenhydramine hydrochloride, chloropheniramine maleate and clemastine; anti-tussive-expectorants, such as codeine phosphate and isoproterenol hydrochloride; analgesics, such as opioids (like diamorphine, morphine and its polar metabolites, such as morphine-6-glucuronides and morphine-3-sulphate); anti-emetics, such as metoclopramide, ondansetron, chlorpromazine; drugs for treatment of epilepsy, such as clonazepam; drugs for treatment of sleeping disorders, such as melatonin; drugs for treatment of asthma, such as salbutamol.

Combinations of the abovementioned therapeutic agents may be employed.

The compositions according to the invention may be administered orally, nasally, vaginally, buccally, rectally, via the eye, or via the pulmonary route, in a variety of pharmaceutically acceptable dosing forms, which will be familiar to those skilled in the art. For example, compositions may be administered via the nasal route as a powder using a nasal powder device, via the pulmonary route using a powder inhaler or metered dose inhaler, via the vaginal route as a powder using a powder device, formulated into a vagina suppository or pessary or vaginal tablet or vaginal gel, via the buccal route formulated into a tablet or a buccal patch, via the rectal route formulated into suppositories; via the eye in the form of a powder or a dry ointment, and via the oral route in the form of a tablet, a capsule or a pellet (which compositions may administer agent via the stomach, the small intestine or the colon), all of which may be formulated in accordance with techniques which are well known to those skilled in the art. The compositions may gel on the mucosa at least to some extent and this may facilitate retention of the composition on the mucosa.

The preferred route of administration is nasal. Devices which may be used to deliver the compositions according to the invention nasally include the Direct Haler®, the Bespak® powder device, the Monopoudre® (Valois) and the Insufflator® (Teijin).

Compositions according to the invention which may be administered orally may be adapted to deliver therapeutic agent to the small intestine or the colonic, especially the proximal colonic, region of the gastrointestinal tract.

Preferably, a means is provided to prevent release of therapeutic agent until the formulation reaches the small intestine or colon. Means which may be employed in order to prevent release until the small intestine is reached are well known to those skilled in the art (see for example dosage forms coated with so-called enteric polymers that do not dissolve in the acidic conditions which exist in the stomach, but dissolve in the more alkaline conditions found in the small intestine of a mammal. Suitable enteric coating materials include modified cellulose polymers and acrylic polymers and in particular those sold under the trademark Eudragit®.) Means which may be employed in order to prevent release until the colon is reached are well known to those skilled in the art. Such materials include cellulose acetate trimellitate (CAT), hydroxypropylmethyl cellulose phthalate (HPMCP), polyvinyl acetate phthalate (PVAP), cellulose acetate phthalate (CAP) and shellac, as described by Healy in his article "Enteric Coatings and Delayed Release", Chapter 7 in *Drug Delivery to the Gastrointestinal Tract*, eds. Hardy et al, Ellis Horwood, Chichester, 1989). Especially preferred materials are methylmethacrylates or copolymers of methacrylic acid and methylmethacrylate. Such materials are available as Eudragit® enteric polymers (Rohm Pharma, Darmstadt, Germany). Such a coating may also suitably comprise a material which is redox-sensitive (e.g. azopolymers which may, for example, consist of a random copolymer of styrene and hydroxyetlyl methacrylate, cross-linked with divinylazobenzene synthesised by free radical polymerisation, or disulphide polymers (see PCT/BE91/00006 and Van den Mooter, Int. J. Pharm. 87, 37(1992)). See also International Patent Application WO 97/05903.

It will be appreciated by those skilled in the art that the site of delivery may also be selectively controlled by varying the thickness of certain of the abovementioned polymer coatings.

It will be well understood by those skilled in the art that further excipients may be employed in formulations comprising the compositions according to the invention. For example, in solid dosing forms, further excipients which may be employed include diluents such as microcrystalline cellulose (e.g. Avicel®, FMC), lactose, dicalcium phosphate and starch(es); disintegrants such as microcrystalline cellulose, starch(es) and cross-linked carboxymethylcellulose; lubricants such as magnesium stearate and stearic acid; granulating agents such as povidone; and release modifiers such as hydroxypropyl methylcellulose and hydroxypropyl cellulose. Suitable quantities of such excipients will depend upon the identity of the active ingredient(s) and the particular dosing form which is used.

If desired, other materials may be included in the composition, for example absorption enhancers. Suitable absorption enhancers include non-ionic surfactants, cyclodextrins, bile salts and, preferably, phospholipids such as lysophosphatidylcholine, lysophosphatidylglycerol and generally those mentioned in WO 88/09163.

According to a further aspect of the invention, there is provided a pharmaceutical formulation in a form suitable for administration to a mucosal surface which comprises a composition according to the invention in a pharmaceutically acceptable dosage form.

Compositions according to the invention have been found to have the advantage that they provide improved transport of polar drugs across mucosal surfaces, such as the nasal cavity, have improved flow properties when compared to prior art compositions, and avoid the need for the use of chemical crosslinking agents.

According to a further aspect of the invention there is thus provided a method for the improved transport of therapeutic agents across (or into) mucosal surfaces (which includes the presentation of vaccines to mucosal surfaces) in mammals, and a method of treating a human or other mammal, which methods comprise administering a composition, as described above, preferably to a mucosal surface of that human or other mammal, for example the vagina, buccal cavity, rectum, lungs, eye, colon, small intestine, stomach or nasal cavity.

The amount of therapeutic agent which may be employed in the compositions according to the invention will depend upon the agent which is used. However, it will be clear to the skilled person that suitable doses of therapeutic agents can be readily determined non-inventively. Suitable doses are in the range 1 μg to 1 g depending upon the therapeutic agent(s) which is/are employed and the route of administration.

The invention is illustrated, but in no way limited, by the following examples with reference to the figures in which.

EXAMPLE 1

Figure 1:
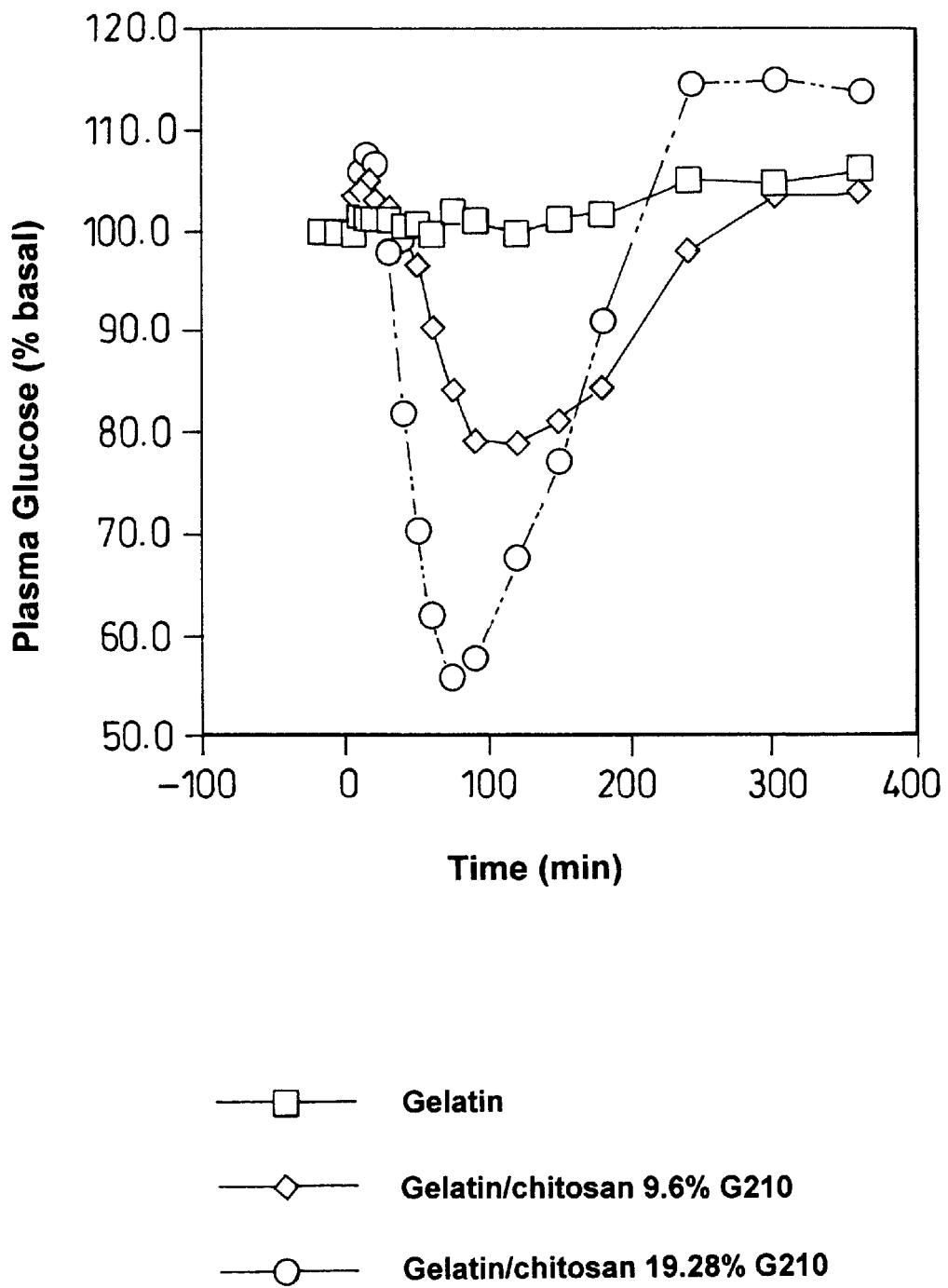
FIG. 1 shows the mean plasma glucose/time curves after administration to sheep of 2 IU/kg insulin in gelatin microspheres and in gelatin/chitosan microspheres containing either 9.6% or 19.28% G210 chitosan glutamate.

Preparation of Microspheres Containing 3.6% w/w Insulin, 86.7% w/w Gelatin A and 9.6% w/w Chitosan Glutamate (Sea Cure G210)

193 mg chitosan glutamate was weighed into a 50 mL beaker and 15 mL of water was added and stirred until dissolution occurred. 1735 mg of gelatin A (Sigma) was added to the chitosan solution and stirred at 40° C. until dissolution occurred. The pH of the solution was adjusted to 4 by adding an appropriate amount of 1M HCl. 72 mg of human zinc insulin (1.8 mL of a 40 mg/mL insulin stock solution) was added to the gelatin/chitosan solution, which was transferred to a 20 mL volumetric flask and water added up to volume.

2 g of Span 80 was weighed into a metal beaker, 200 mL of sunflower oil was added and the mixture warmed to 40° C. The 40° C. insulin/gelatin/chitosan solution was added and emulsified at 1000 rpm for 5 minutes using a Heidolph stirrer fitted with a four blade stirrer arm maintaining the temperature at 40° C. The beaker was transferred to an ice bath and stirring continued at 1000 rpm until the temperature had dropped to below 10° C. The stirring speed was reduced to 500 rpm, 150 mL of chilled acetone was added to the emulsion at 5 ml/min, and the mixture was then centrifuged at 2500 rpm in centrifuge tubes for 10 min. The supernatant was discarded and the pellet resuspended in 50 mL acetone. The microspheres were recovered by vacuum filtration and washing with further 50 mL of chilled acetone. The filter cake was allowed to dry and the microspheres placed in 50 mL of acetone in a screw capped bottle containing a magnetic stirrer and stirred overnight. The microspheres were vacuum filtered and dried in a desiccator.

EXAMPLE 2

Preparation of Microspheres Containing 3.6% w/w Insulin, 77.12% w/w Gelatin A and 19.28% w/w Chitosan Glutamate (Sea Cure G210)

386 mg of chitosan glutamate was weighed into a 50 mL beaker, 15 mL of water was added and the resultant stirred until dissolution occurred. 1542 mg of gelatin A was added to the chitosan solution, which was then stirred at 40° C. until dissolution occurred. The pH of the solution was adjusted to 4 by adding an appropriate amount of 1M HCl. 72 mg of human zinc insulin (1.8 mL of a 40 mg/mL insulin stock solution) was added to the gelatin/chitosan solution, which was then transferred to a 20 mL volumetric flask, and water was added up to volume.

2 g of Span 80 was weighed into a metal beaker, 200 mL of sunflower oil was added and the mixture warmed to 40° C. The 40° C. insulin/gelatin/chitosan solution was added and emulsified at 1000 rpm for 5 minutes using a Heidolph stirrer fitted with a four blade stirrer arm maintaining the temperature at 40° C. The beaker was transferred to an ice bath and stirring continued at 1000 rpm until the temperature had dropped to below 10° C. The stirring speed was reduced to 500 rpm and 150 mL of chilled acetone was added to the emulsion at 5 mL/min which was then centrifuged at 2500 rpm in centrifuge tubes for 10 min. The supernatant was discarded and the pellet resuspended in 50 mL acetone. The microspheres were recovered by vacuum filtration and washed with further 50 mL of chilled acetone. The filter cake was allowed to dry, the microspheres placed in 50 mL of acetone in a screw capped bottle containing a magnetic stirrer and stirred overnight. The microspheres were vacuum filtered and dried in a desiccator.

EXAMPLE 3

Preparation of Microspheres Containing 0.2% w/w Salmon Calcitonin (SCT), 59.9% w/w Gelatin A and 39.9% w/w Chitosan Glutamate (Sea Cure G110)

798 mg chitosan glutamate (G110) was weighed into a 50 mL beaker, 15 mL of water was added and the resultant stirred until dissolution occurred. 1198 mg of gelatin A was added to the chitosan solution, which was then stirred at 40° C. until dissolution occurred. The pH of the solution was adjusted to 4 by adding an appropriate amount of 1M HCl. 20,000 IU of SCT (0.91 mL of a 4 mg/mL SCT stock solution) was added to the gelatin/chitosan solution which was transferred to a 20 mL volumetric flask, and water was added up to volume.

2 g of Span 80 was weighed into a metal beaker, 200 mL of sunflower oil was added and the mixture warmed to 40° C. The 40° C. SCT/gelatin/chitosan solution was added and emulsified at 1000 rpm for 5 minutes using a Heidolph stirrer fitted with a four blade stirrer arm maintaining the temperature at 40° C. The beaker was transferred to an ice bath and stirring continued at 1000 rpm until the temperature had dropped to below 10° C. The stirring speed was reduced to 500 rpm, 150 mL of chilled acetone was added to the emulsion at 5 mL/min which was then centrifuged at 2500 rpm in centrifuge tubes for 10 min. The supernatant was discarded and the pellet resuspended in 50 mL acetone. The microspheres were recovered by vacuum filtration and washed with a further 50 mL of chilled acetone. The filter cake was allowed to dry and the microspheres placed in 50 mL of acetone in a screw capped bottle containing a magnetic stirrer and stirred overnight. The microspheres were vacuum filtered and dried in a desiccator.

EXAMPLE 4

Preparation of Microspheres Containing 0.2% w/w SCT, 79.9% w/w Gelatin A and 19.9% w/w Chitosan Glutamate (Sea Cure G210)

398 mg chitosan glutamate (G210) was weighed into a 50 mL beaker, 15 mL of water was added and the resultant mixture stirred until dissolution occurred. 1598 mg of gelatin A was added to the chitosan solution, which was stirred at 40° C. until dissolution occurred. The pH of the solution was adjusted to 4 by adding an appropriate amount of 1M HCl. 20,000 IU of SCT (0.91 mL of a 4 mg/mL SCT stock solution) was added to the gelatin/chitosan solution, which was then transferred to a 20 mL volumetric flask and water was added up to volume.

2 g of Span 80 was weighed into a metal beaker, 200 mL of sunflower oil was added and the mixture was warmed to 40° C. The 40° C. insulin/gelatin/chitosan solution was added and emulsified at 1000 rpm for 5 minutes using a Heidolph stirrer fitted with a four blade stirrer arm, maintaining the temperature at 40° C. The beaker was transferred to an ice bath and stirring continued at 1000 rpm until the temperature had dropped to below 10° C. The stirring speed was reduced to 500 rpm, 150 mL of chilled acetone was added to the emulsion at 5 mL/min which was then centrifuged at 2500 rpm in centrifuge tubes for 10 min. The supernatant was discarded and the pellet resuspended in 50 mL acetone. The microspheres were recovered by vacuum filtration and washed with a further 50 mL of chilled acetone. The filter cake was allowed to dry and the microspheres placed in 50 mL of acetone in a screw capped bottle containing a magnetic stirrer and stirred overnight. The microspheres were vacuum filtered and dried in a desiccator.

EXAMPLE 5

The insulin-chitosan/gelatin microsphere formulations from Examples 1 and 2 were administered nasally to sheep and the effect of the formulations was compared to the effect of administering insulin in gelatin A microspheres The insulin—gelatin microspheres were prepared in the following way: 1928 mg gelatin A was added to 14 mL of water in a 50 mL beaker and heated under stirring at 40° C. until the gelatin had dissolved. The pH of the gelatin solution was adjusted to 4 using 1M HCl and an equivalent of 72 mg of human zinc insulin (1.8 mL of 40 mg/mL insulin stock solution) was added to the solution. The solution was transferred to a 20 mL volumetric flask and made up to volume. 2 g of Span 80 was weighed into a metal beaker, 200 mL of sunflower oil was added and the mixture warmed to 40° C. The 40° C. insulin/gelatin solution was added and emulsified at 1000 rpm for 5 minutes using a Heidolph stirrer fitted with a four blade stirrer arm, with the temperature maintained at 40° C. The beaker was transferred to an ice bath and stirring continued at 1000 rpm until the temperature had dropped to below 10° C. The stirring speed was reduced to 500 rpm and 150 mL of chilled acetone was added to the emulsion at 5 mL/min. The emulsion was centrifuged at 2500 rpm in centrifuge tubes for 10 min., the supernatant discarded and the pellet resuspended in 50 mL acetone. The microspheres were recovered by vacuum filtration and washed with further 50 mL of chilled acetone. The filter cake was allowed to dry and the microspheres were placed in 50 mL of acetone in a screw capped bottle containing a magnetic stirrer and stirred overnight. The microspheres were vacuum filtered and dried in a desiccator.

Figure 2:
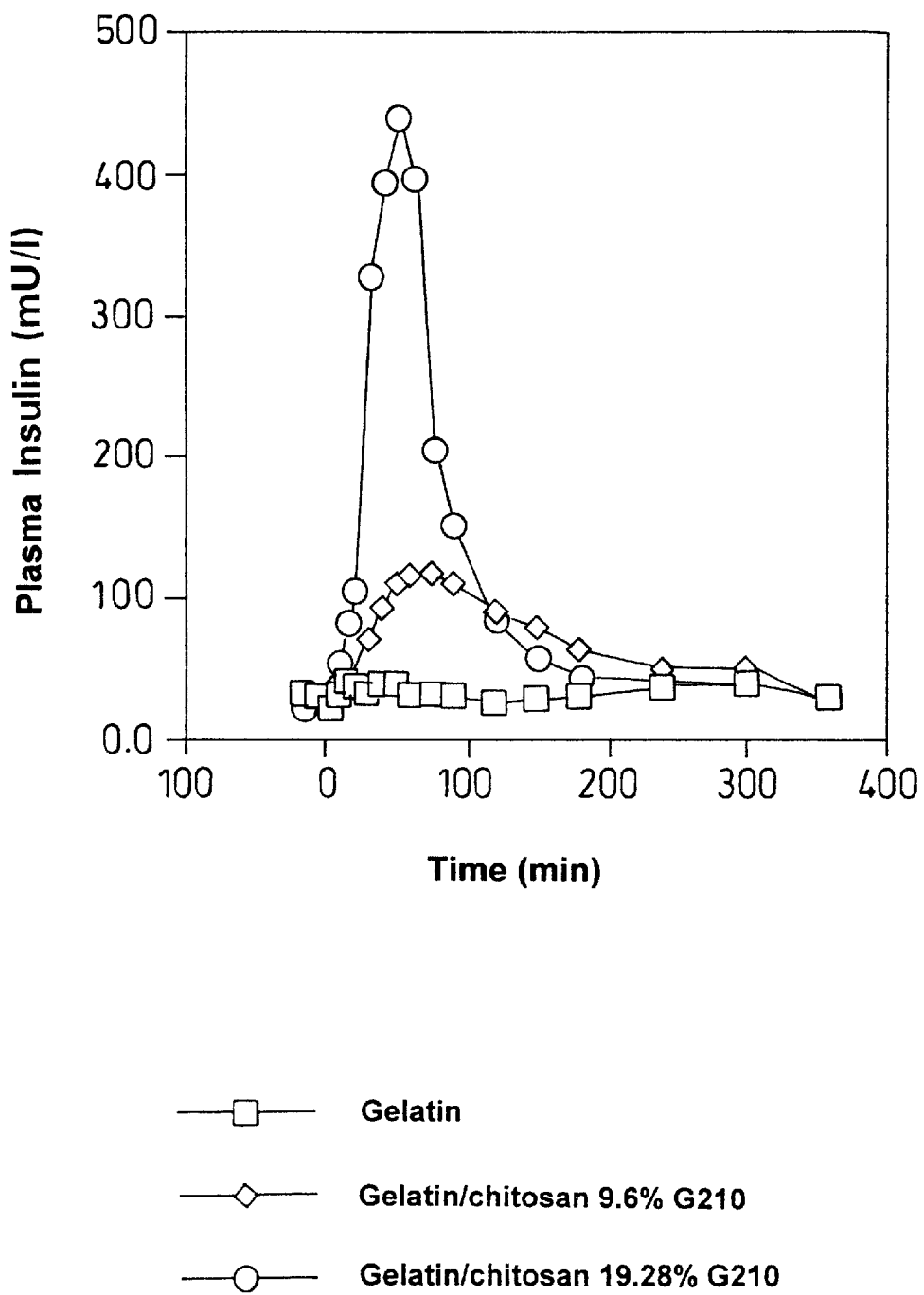
FIG. 2 shows the mean plasma insulin/time curves after administration to sheep of 2 IU/kg insulin in gelatin microspheres and in gelatin/chitosan microspheres containing either 9.6% or 19.28% G210 chitosan glutamate.

Each of the microsphere formulations were administered nasally to groups of five sheep using blueline siliconised tubes at an insulin dose of 2 IU/kg and a microsphere dose of 2.0 mg/kg. Blood samples were collected at specified time points from the cannulated external jugular veins and plasma glucose and insulin concentrations measured. The mean changes in plasma glucose concentration with time for the three formulations are shown in FIG. 1. It can be seen that insulin given nasally in combination with gelatin microspheres did not result in any significant lowering of the plasma glucose levels ($C_{min}$=95.9%) whereas the formulations containing 9.6% chitosan and 19.28% chitosan gave glucose lowering effects of $C_{min}$=74.6% and $C_{min}$=53.8% of basal level, respectively. The corresponding plasma insulin levels for the three formulations are shown in FIG. 2. It can be seen that $C_{max}$ for both the chitosan/gelatin microsphere formulations (131.6 mU/L and 439.7 mU/L for the 9.6/86.7% and 19.28/77.12% chitosan/gelatin microsphere, respectively) were significantly higher than the $C_{max}$, seen for the gelatin microspheres (53.5 mU/L).

EXAMPLE 6

The calcitonin-chitosan/gelatin microsphere formulations described in Example 3 and 4 were administered nasally to sheep and the effect of the formulations compared to the effect of administering calcitonin in gelatin microspheres.

The calcitonin—gelatin microspheres were prepared in the following way: 1996 mg gelatin A was added to 15 mL of water in a 50 mL beaker and heated under stirring at 40° C. until the gelatin had dissolved. The pH of the gelatin solution was adjusted to 4 using 1M HCl and an equivalent of 20,000 IU of salmon calcitonin (0.91 mL of 4 mg/mL SCT stock solution) was added to the solution. The solution was transferred to a 20 mL volumetric flask and made up to volume. 2 g of Span 80 was weighed into a metal beaker, 200 mL of sunflower oil was added and the mixture warmed to 40° C. The 40° C. insulin/gelatin solution was added and emulsified at 1000 rpm for 5 minutes using a Heidolph stirrer fitted with a four blade stirrer arm, with the temperature maintained at 40° C. The beaker was transferred to an ice bath and stirring continued at 1000 rpm until the temperature had dropped to below 10° C. The stirring speed was reduced to 500 rpm and 150 mL of chilled acetone was added to the emulsion at 5 mL/min. The emulsion was centrifuged at 2500 rpm in centrifuge tubes for 10 min., the supernatant was discarded and the pellet resuspended in 50 mL acetone. The microspheres were recovered by vacuum filtration and washed with further 50 mL of chilled acetone. The filter cake was allowed to dry and the microspheres placed in 50 mL of acetone in a screw capped bottle containing a magnetic stirrer and stirred overnight. The microspheres were vacuum filtered and dried in a desiccator.

Figure 3:
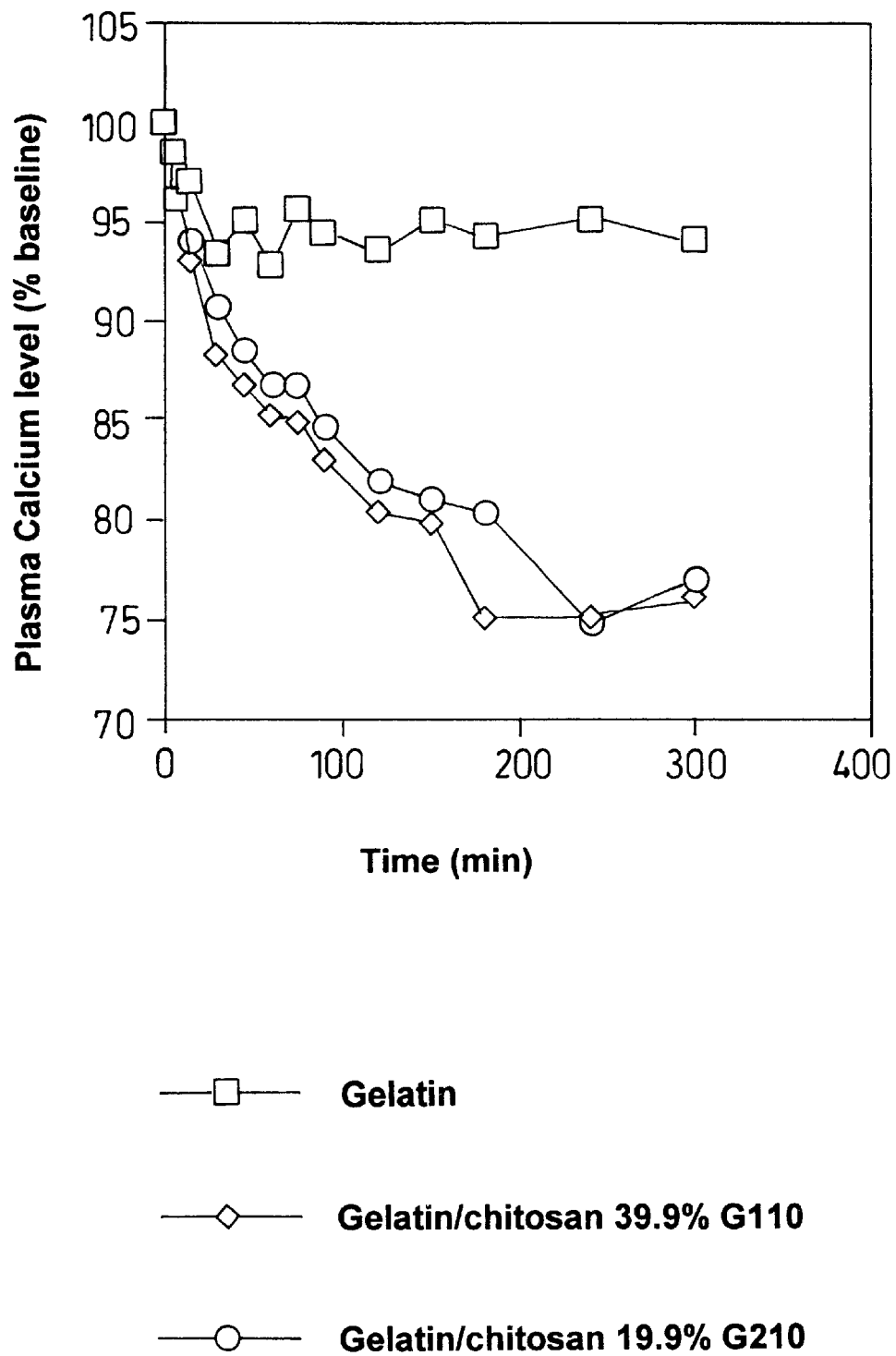
FIG. 3 shows the mean plasma calcium/time curves after administration to sheep of 20 IU/kg salmon calcitonin in gelatin microspheres and in gelatin/chitosan microspheres containing either 39.9% G110 or 19.9% G210 chitosan glutamate.

Each of the microsphere formulations were administered nasally to groups of five sheep using blueline siliconised tubes at an SCT dose of 20 IU/kg and a microsphere dose of 2.004 mg/kg. Blood samples were collected at specified time points from the cannulated external jugular veins and plasma calcium concentrations measured. The mean changes in plasma calcium concentration with time for the three formulations are shown in FIG. 3. It can be seen that SCT given nasally in combination with gelatin microspheres only resulted in a minimal lowering of the plasma calcium levels ($C_{min}$=91.1%) whereas the formulations containing 39.9% G110 chitosan and 19.9% G210 chitosan gave calcium lowering effects of $C_{min}$=73.6% and $C_{min}$=74.7% of basal level, respectively. There was no significant difference between the effects obtained for the 39.9% G110 and 19.9% G210 chitosan levels in the gelatin microspheres.

EXAMPLE 7

The insulin-chitosan/gelatin microsphere formulation described in Example 2 was administered nasally to sheep and the effect of the formulation compared to the effect of administering insulin in a simple chitosan solution.

Figure 4:
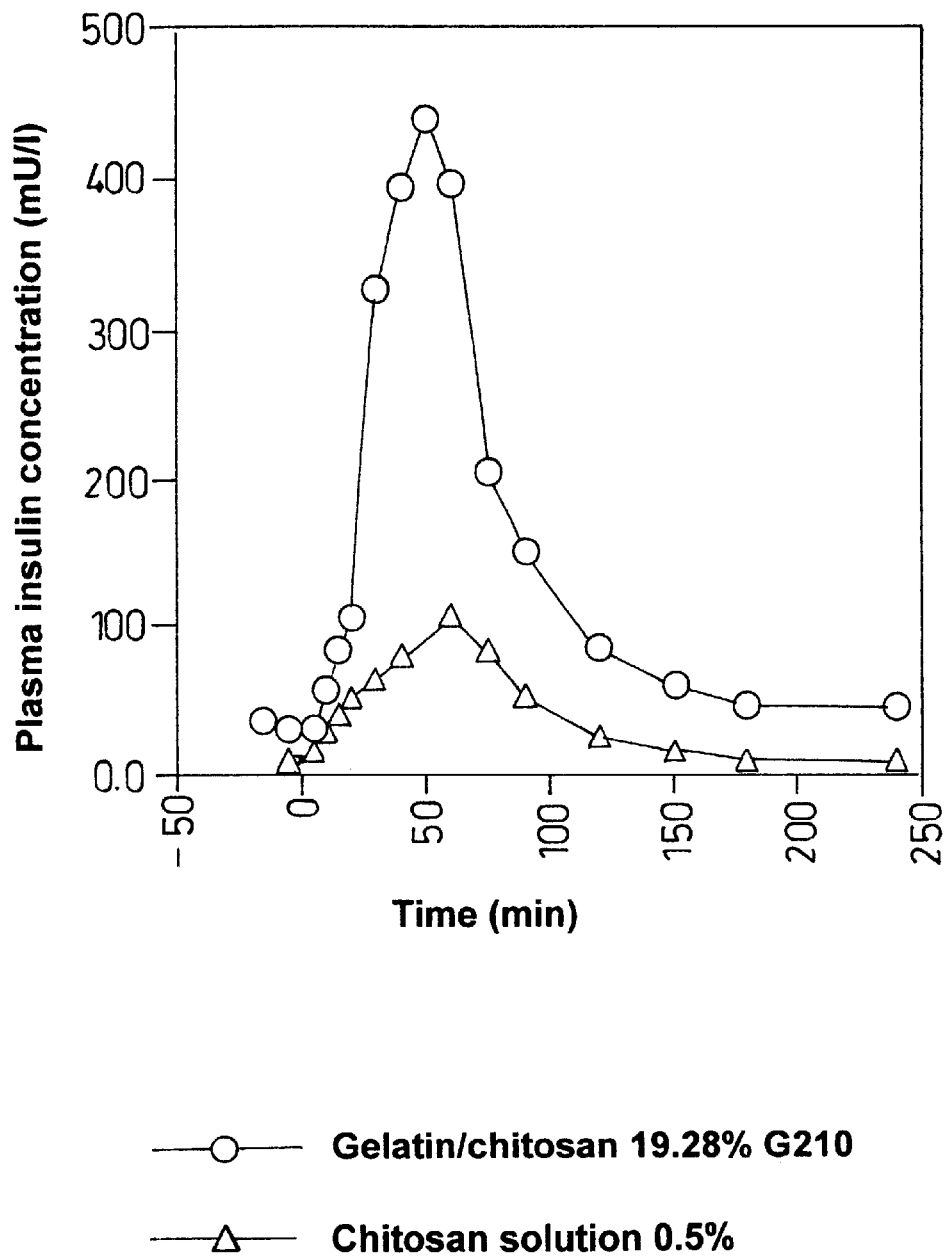
FIG. 4 shows the mean plasma insulin/time curves after administration to sheep of 2 IU/kg insulin in 0.5% chitosan solution (G210) and in gelatin/chitosan microspheres containing 19.28% G210 chitosan glutamate.

The microsphere formulation was administered nasally to a group of five sheep using blueline siliconised tubes at an insulin dose of 2 IU/kg and a microsphere dose of 2.0 mg/kg. As a comparison, a solution of 200 IU/mL insulin in 5 mg/mL G210 chitosan glutamate solution was administered nasally at 2 IU/kg to a group of four sheep. Blood samples were collected at specified time points from the cannulated external jugular veins and plasma insulin concentrations measured. The mean changes in plasma insulin concentration with time for the two formulations are shown in FIG. 4. It can be seen that the plasma insulin level is significantly higher for the gelatin/chitosan microsphere formulation ($C_{max}$=450 mU/L) as compared to the chitosan solution formulation ($C_{max}$=100 mU/L).

EXAMPLE 8

The insulin-chitosan/gelatin microsphere formulation described in Example 2 was administered nasally to sheep and the effect of the formulation compared to the effect of administering insulin with a chitosan powder formulation.

Figure 5:
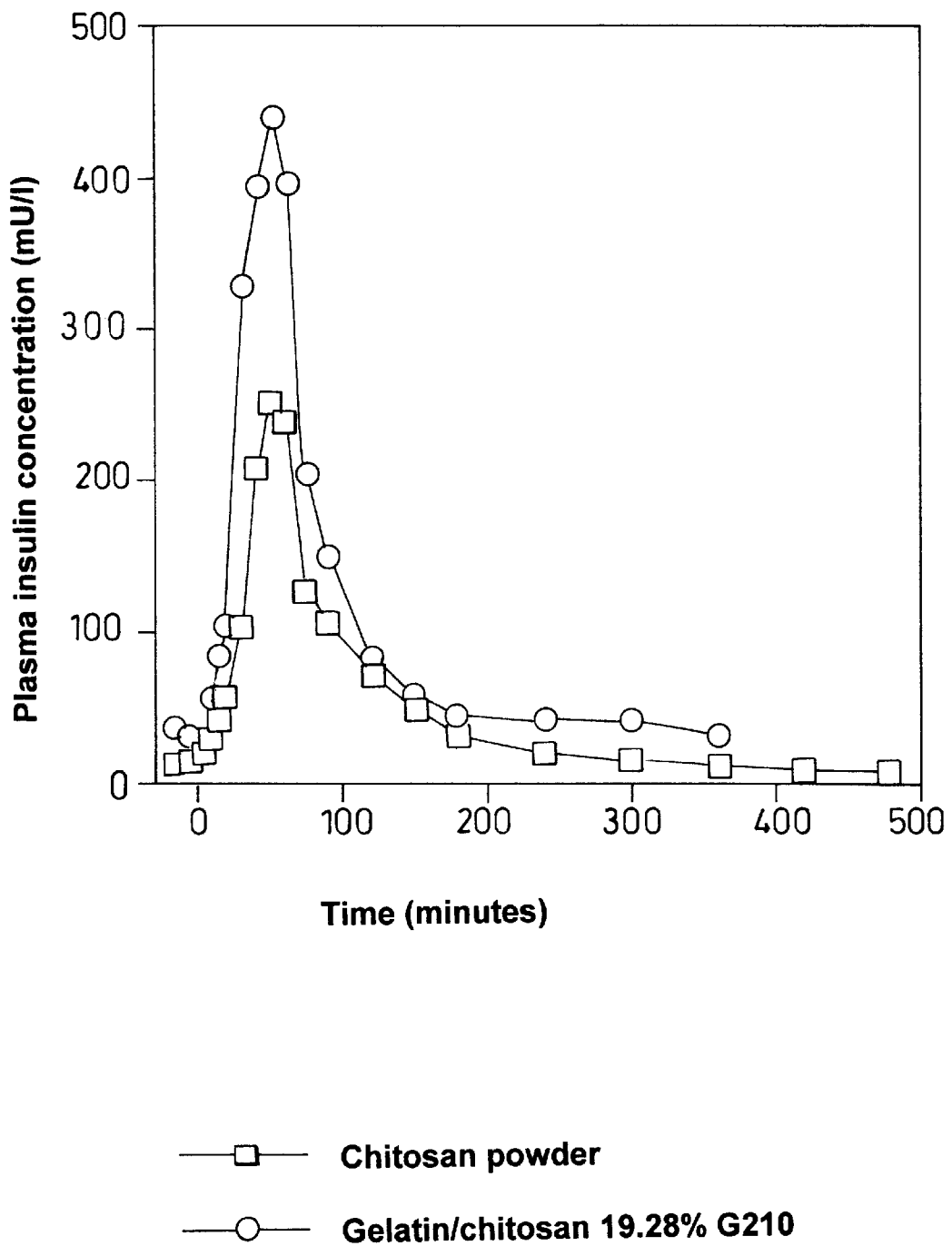
FIG. 5 shows the mean plasma insulin/time curves after administration to sheep of 2 IU/kg insulin with chitosan powder (G210) and in gelatin/chitosan microspheres containing 19.28% G210 chitosan glutamate.

The gelatin/chitosan microsphere formulation was administered nasally to a group of five sheep using blueline siliconised tubes at an insulin dose of 2 IU/kg and a microsphere dose of 2.0 mg/kg. As a comparison, a mixture of 640 IU insulin with 800 mg G210 chitosan glutamate was administered nasally at 2 IU/kg to a group of four sheep at 2 IU/kg. Blood samples were collected at specified time points from the cannulated external jugular veins and plasma insulin concentrations measured. The mean changes in plasma insulin concentration with time for the two formulations are shown in FIG. 5. It can be seen that the plasma insulin level is significantly higher for the gelatin/chitosan microsphere formulation ($C_{max}$=450 mU/L) as compared to the chitosan powder formulation ($C_{max}$250 mU/L). It should also be noted that the amount of chitosan administered in the two formulations is much higher for the chitosan powder formulation than for the gelatin/chitosan microsphere formulation.

EXAMPLE 9
Preparation of Microspheres Containing 0.4% w/w PTH, 19.92%, w/w Chitosan Glutamate (Sea Cure 210) and 79.68% w/w Gelatin A 9.28 mg of PTH was added to 20 mL of a solution containing 400 mg chitosan glutamate and 1.6 g of gelatin A and maintained at 50–60° C. 2 g of Span 80 was weighed into a beaker and 200 mL of soya oil was added. The resultant was mixed and heated to 40° C. The PTH/chitosan/gelatin solution was added and emulsified at 1000 rpm for 10 min. using a Heidolph stirrer fitted with a four blade stirrer arm, maintaining the temperature at 40° C. The beaker was transferred to an ice bath and stirring continued at 100 rpm until the temperature had dropped to below 10° C. The stirring speed was reduced to 500 rpm and 150 mL of chilled acetone was added to the emulsion at 5 mL/min, followed by centrifugation at 3000 rpm for 10 min. The supernatant was discarded and the pellet resuspended in acetone. The microspheres were recovered by vacuum filtration and washed with 50 mL of chilled acetone. The filter cake was allowed to dry, the microspheres placed in 50 mL of acetone in a screw capped bottle containing a magnetic stirrer and stirred overnight. The microspheres were vacuum filtered and dried in a dissector.

Sheep Study

Figure 6:
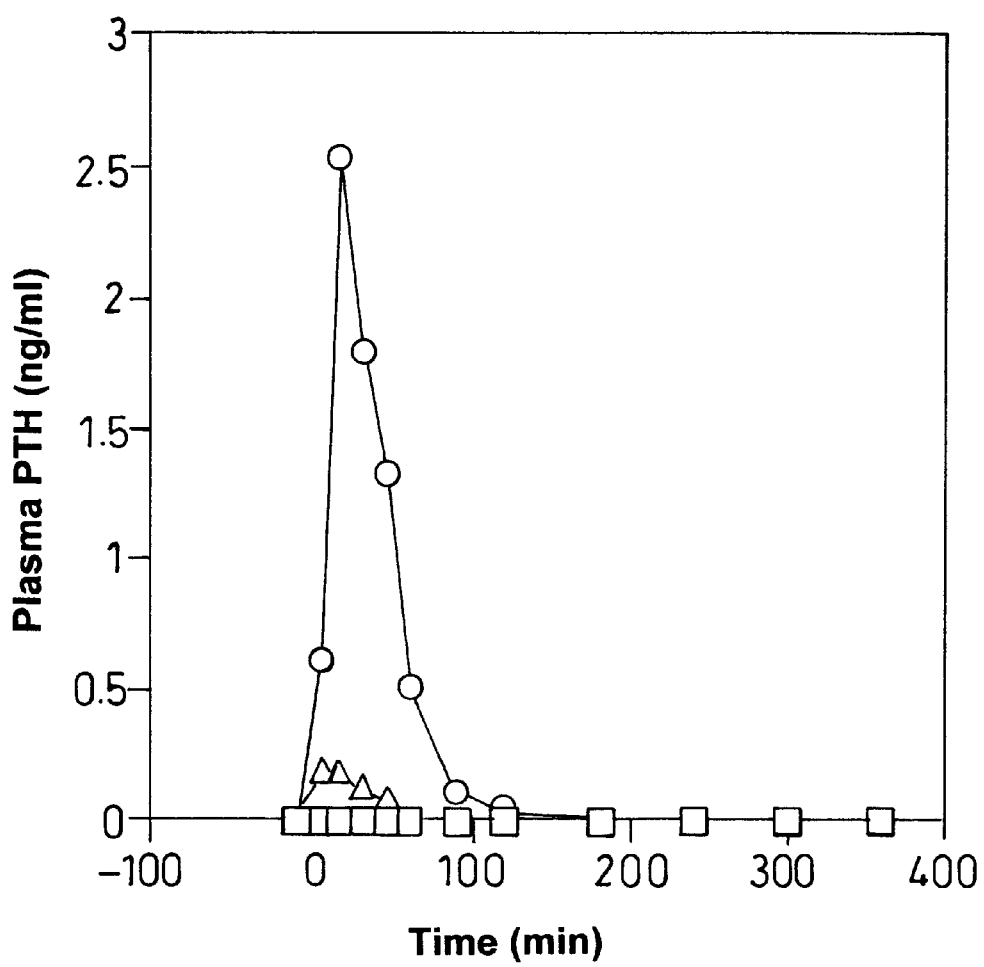
FIG. 6 shows the mean changes in plasma PTH concentration for a PTH/gelatin/chitosan microsphere formulation (PTH CHI/GER) as compared to a formulation comprising PTH (alone) in saline (PTH sol) and PTH with chitosan glutamate (PTH CHI Sol).

The PTH gelatin/chitosan microsphere formulation was administered nasally to a group of 6 sheep using blueline siliconised tubes at a PTH dose of 4 µg/kg. As a comparison, the same group of sheep was also administered the same dose of PTH in saline and in saline containing 0.5% chitosan glutamate. Blood samples were collected at specified time points from the cannulated external jugular veins and plasma PTH concentrations measured. The mean changes in plasma PTH concentration with time for the three formulations are shown in FIG. 6. It can be seen that the plasma PTH is significantly higher for the gelatin in chitosan microsphere formulation ($C_{max}$=2.5 ng/mL) as compared to the chitosan solution formulation ($C_{max}$=0.25 ng/mL) and the control PTH solution ($C_{max}$=0 ng/mL).

EXAMPLE 10
Determination of Hausner Ratio for Chitosan/Gelatin A Microspheres and For Spray Dried Chitosan Microspheres (Sea Cure G210)

A known weight (see below) of chitosan/gelatin microspheres, prepared as in Example 2, was carefully poured into a 10 mL measuring cylinder and the volume recorded (poured volume). The measuring cylinder was tapped (onto the bench) 50 times and the volume of the chitosan/gelatin microspheres again recorded (tapped volume). The measurement was carried out in triplicate.

| Weight | Poured Vol.(cm³) | Poured Den.(g/cm³) | Tapped Vol.(cm³) | Tapped Den. (g/cm³) | Hausner Ratio |
|---|---|---|---|---|---|
| 2.2481 | 7.3 | 0.3079 | 5.8 | 0.3876 | 1.26 |
| 2.3680 | 7.6 | 0.3116 | 6.0 | 0.3947 | 1.27 |
| 2.3220 | 7.5 | 0.3096 | 6.1 | 0.3807 | 1.23 |

Hausner Ratio (chitosan/gelatin microspheres) = 1.25 (good flow porperties)

A known weight (see below) of spray dried chitosan microparticles (Sea Cure G210; Pronova) was carefully poured into a 10 mL measuring cylinder and the volume recorded (poured volume). The measuring cylinder was tapped (onto the bench) 50 times and the volume of the chitosan again recorded (tapped volume). The measurement was carried out in triplicate.

| Weight | Poured Vol.(cm³) | Poured Den.(g/cm³) | Tapped Vol.(cm³) | Tapped Den. (g/cm³) | Hausner Ratio |
|---|---|---|---|---|---|
| 1.5609 | 9.0 | 0.1734 | 4.1 | 0.3807 | 2.20 |
| 1.4728 | 8.5 | 0.1733 | 3.8 | 0.3876 | 2.24 |
| 1.4004 | 8.0 | 0.1751 | 3.6 | 0.3890 | 2.22 |

Hausner Ratio (chitosan) = 2.22 (very poor flow properties)

EXAMPLE 11
Determination of Angle of Repose For Chitosan/Gelatin A Microspheres and for Spray Dried Chitosan Microspheres (Sea Cure G210)

The Angle of Repose (θ) was determined by pouring about 3 g of chitosan/gelatin microspheres, prepared as in Example 2, through a funnel (held at a fixed height) onto a piece of graph paper until a cone was formed. The height (H) and the radius (R) of the cone were determined and the Angle calculated (tan θ=H/R). The measurement was carried out in triplicate.

Mean Height=10 mm
Mean Radius=18 mm
Angle of Repose (chitosan/gelatin microspheres)=29° (good flow properties)

The Angle of Repose (θ) was determined by pouring about 3 g of spray dried chitosan microparticles (Sea Cure G210; Pronova) through a funnel (held at a fixed height) onto a piece of graph paper until a cone was formed. The height (H) and the radius (R) of the cone were determined and the Angle calculated (tanθ=H/R). The measurement was carried out in triplicate.

Mean Height=25 mm
Mean Radius=24 mm
Angle of Repose (chitosan)=46° (very poor flow properties).

EXAMPLE 12
Determination of the Effect of Dose of Microspheres on the Absorption of Insulin Microspheres were prepared as in Example 2 with the final concentration of insulin in the microspheres being 2.0%, 4.0%, 5.3%, 7.7% and 14.4% w/w.

Figure 7:
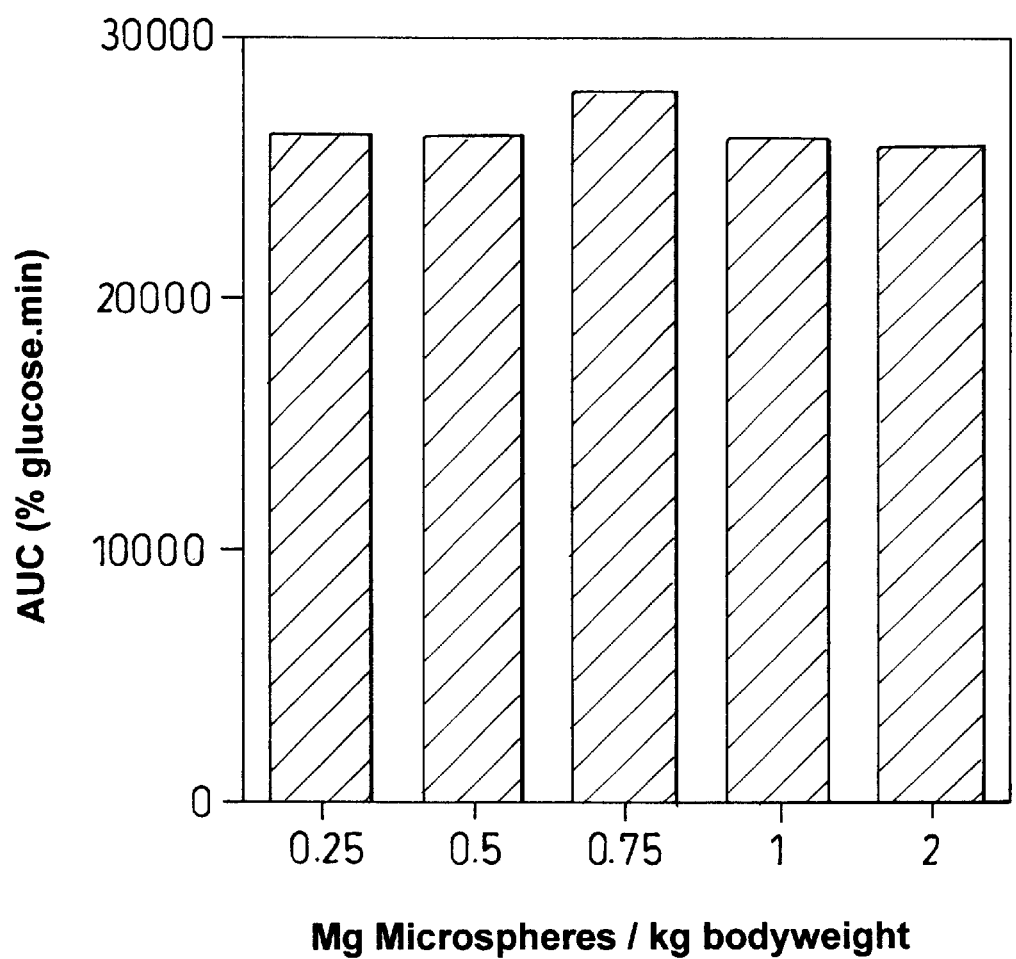
FIG. 7 shows the effect on plasma glucose level of gelatin/chitosan microspheres comprising different amounts of insulin.

The microspheres were administered nasally to groups of 4 sheep with a fixed dose of 1 IU insulin/kg and 2.0, 1.0, 0.75, 0.5 and 0.25 mg/kg of gelatin/chitosan microspheres as described in Example 8. The mean changes in plasma glucose level expressed as AUC are given in FIG. 7. It can be seen that the effect of the gelatin/chitosan microspheres on the AUC is no different whether 2.0 mg/kg or down to 0.25 mg/kg of microspheres are administered with a constant dose of insulin.

Figure 8:
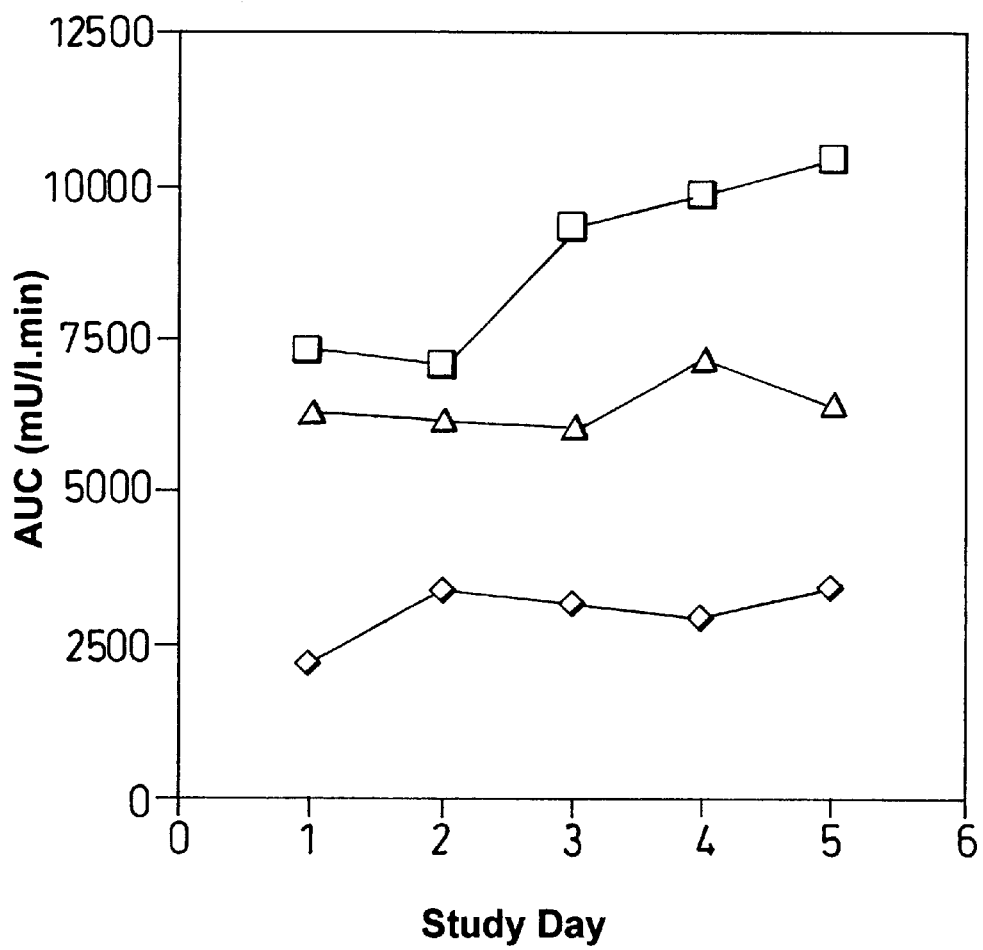
FIG. 8 shows the effect of repeated administration of gelatin/chitosan microspheres on plasma insulin level.

EXAMPLE 13
Effect of Repeated Administration of Gelatin A/Chitosan Microspheres on Plasma Insulin Level Gelatin/chitosan/insulin microspheres were prepared as in Example 2. The microspheres and a chitosan solution formulation, prepared as in Example 8, were administered nasally to groups of 4 sheep once daily for 5 consecutive days. A SC injection of insulin solution was given to the third group of sheep for five consecutive days. Plasma insulin levels expressed as AUC are given in FIG. 8. It can be seen that the AUC obtained for each day is consistently higher for the gelatin/chitosan microsphere formulation as compared to the chitosan solution formulation. It can also be seen that the AUCs obtained on the five consecutive days are similar for the nasal formulation, thus showing a consistent and reproducible effect, whereas a certain accumulative effect can be seen for the SC repeated injection.

We claim:

1. A composition comprising
   a mixture of chitosan and type A, cationic, gelatin having an isoelectric point between pH 7 and 9; and
   a therapeutic agent.
2. The composition of claim 1 wherein the composition is in the form of microparticles.
3. The composition of claim 2 wherein the therapeutic agent is incorporated into the microparticles during production of the microparticles, adsorbed to the surface of the microparticles, or is present as an admixture with the microparticles.
4. The composition of claim 2 wherein the microparticles are microspheres.
5. The composition of claim 1 wherein the composition is suitable for delivery of the therapeutic agent across a mucosal membrane into the systemic circulation.
6. The composition of claim 1 wherein the chitosan has a molecular weight greater than 4000 Dalton.
7. The composition of claim 6 wherein the chitosan has a molecular weight in the range 25,000 to 2,000,000 Dalton.
8. The composition of claim 7 wherein the chitosan has a molecular weight in the range 50,000 to 30,000 Dalton.
9. The composition of claim 1 wherein the chitosan is a derivative formed by bonding of acyl or alkyl groups with the hydroxyl moieties of the chitosan.
10. The composition of claim 1 wherein the chitosan is in the form of a salt selected from the group consisting of nitrates, phosphates, sulfates, hydrochloride, glutamates, lactate and acetate.
11. The composition of claim 2 wherein the microparticles are produced by a process selected from the group consisting of spray drying, emulsification, solvent evaporation, and precipitation.
12. The composition of claim 1 wherein the chitosan has a degree of deacetylation of greater than 40%.
13. The composition of claim 12 wherein the degree of deacetylation is between 50 and 98%.
14. The composition of claim 13 wherein the degree of deacetylation is between 70 and 90%.
15. The composition of claim 2 wherein the microparticles have a diameter of between 1 and 200 microns.
16. The composition of claim 15 wherein the diameter is between 1 and 100 microns.
17. The composition of claim 1 comprising between 50 and 95% of type A gelatin.
18. The composition of claim 17 comprising between 75 and 85% of type A gelatin.
19. The composition of claim 1 wherein the therapeutic agent is a polar drug.
20. The composition of claim 1 wherein the therapeutic agent is a polypeptide.
21. The composition of claim 20 wherein the therapeutic agent is selected from the group consisting of insulin, calcitonin, luteinising hormone releasing hormone, growth hormones, and growth hormone releasing factors.
22. The composition of claim 1 wherein the therapeutic agent is an analgesic agent or a drug for the treatment of migraine.
23. The composition of claim 1 wherein the therapeutic agent is an antigen intended for mucosal immunisation.
24. The composition of claim 1 wherein the therapeutic agent is a gene or gene construct (DNA) intended for the transfection of cells in the mucosal surface.
25. The composition of claim 1 further comprising an absorption enhancing agent.
26. The composition of claim 25 wherein the absorption enhancing agent is a phospholipid.
27. The composition of claim 1 in a pharmaceutically acceptable dosage form suitable for administration to a mucosal surface.
28. A method for the improved transport of a therapeutic agent across a mucosal surface in a mammal, comprising
   administering a composition comprising (a) a mixture of chitosan and type A cationic, gelatin, and (b) the therapeutic agent, to a mucosal surface of the mammal.
29. The composition of claim 27 for oral administration wherein the mucosal surface is in the gastrointestinal tract.
30. The method of claim 28 wherein the mucosal surface is selected from nasal mucosa, buccal cavity, vaginal mucosa, rectal mucosa, an eye, a lung, and gastrointestinal tract.
31. A method of treating a mammalian patient comprising
   administering to the patient a composition comprising (a) a mixture of chitosan and type A, cationic, gelatin having an isoelectric point between pH 7 and 9, and (b) therapeutic agent.
32. The method of claim 31 wherein the composition is delivered to a mucosal surface.
33. The method of claim 31 wherein the composition is adapted to deliver the therapeutic agent across a mucosal membrane into the systemic circulation.
34. A method for making microparticles of type A gelatin and chitosan comprising
   spray drying a mixture of chitosan and Type A, cationic gelatin having an isoelectric point between pH 7 and 9 to form the microparticles.
35. A method for making microparticles of type A gelatin and chitosan comprising
   mixing a solution of chitosan with type A, cationic gelatin having an isoelectric point between pH 7 and 9, which is warmed to melt the gelatin, to form a mixture;
   emulsifying the mixture in a medium to form an emulsion comprising microparticles of the mixture; and
   cooling the emulsion to solidify the microparticles.
36. The method of claim 35 wherein the chitosan is dissolved in water and mixed with the gelatin under heating to 40° C.
37. The method of claim 35 wherein the mixture is emulsified in the presence of an emulsifier, at a temperature above the melting point of the gelatin, wherein the medium is an organic medium.
38. The method of claim 35 wherein the microparticles are solidified by decreasing the temperature of the emulsion below 10° C.

39. The method of claim 35 wherein the microparticles further comprise a therapeutic agent, the method further comprising incorporating the therapeutic agent into the mixture before emulsification.

40. The method of claim 34 wherein the microparticles further comprise a therapeutic agent, the method further comprising freeze drying or spray drying a suspension of the formed microparticles with the therapeutic agent, so that the agent is adsorbed onto the surface of the microparticles.

41. The method of claim 34 wherein the microparticles further comprise a therapeutic agent, the method further comprising physically or mechanically mixing the formed microparticles with the therapeutic agent, so that the therapeutic agent is adsorbed onto the surface of the microparticles.

42. The method of claim 35 wherein the microparticles further comprise a therapeutic agent, the method further comprising freeze drying or spray drying a suspension of the solidified microparticles with the therapeutic agent so that the therapeutic agent is adsorbed onto the surface of the microparticles.

43. The method of claim 35 wherein the microparticles further comprise a therapeutic agent, the method further comprising isolating and drying the solidified microparticles and then physically or mechanically mixing the microparticles with the therapeutic agent so that the therapeutic agent is adsorbed onto the surface of the microparticles.

* * * * *

UNITED STATES PATENT AND TRADEMARK OFFICE
CERTIFICATE OF CORRECTION

PATENT NO. : 6,465,626 B1
DATED : October 15, 2002
INVENTOR(S) : Peter James Watts et al.

It is certified that error appears in the above-identified patent and that said Letters Patent is hereby corrected as shown below:

Column 14,
Lines 9-10, replace "porperties", with -- properties --.

Column 15,
Lines 41-42, replace "30,000" with -- 300,000 --.

Signed and Sealed this

Thirty-first Day of August, 2004

JON W. DUDAS
*Director of the United States Patent and Trademark Office*